(12) United States Patent
Zelnik et al.

(10) Patent No.: US 7,555,794 B2
(45) Date of Patent: Jul. 7, 2009

(54) METHODS AND APPARATUS FOR ERGONOMIC ARM AND HEAD SUPPORT

(75) Inventors: Deborah Ruth Zelnik, Haifa (IL); Pascal Salazar-Ferrer, Eden Prairie, MN (US); Danny Hausner, Haifa (IL)

(73) Assignee: GE Medical Systems Israel, Ltd., Tel Aviv (IL)

( * ) Notice: Subject to any disclaimer, the term of this patent is extended or adjusted under 35 U.S.C. 154(b) by 208 days.

(21) Appl. No.: 11/490,612

(22) Filed: Jul. 21, 2006

(65) Prior Publication Data

US 2007/0053502 A1 Mar. 8, 2007

Related U.S. Application Data

(60) Provisional application No. 60/710,709, filed on Aug. 23, 2005.

(51) Int. Cl.
*A47G 9/00* (2006.01)

(52) U.S. Cl. .................. 5/632; 5/601; 5/636; 5/643; 5/646

(58) Field of Classification Search ............ 5/601, 5/636, 643, 646, 647, 632; 128/845; 378/209
See application file for complete search history.

(56) References Cited

U.S. PATENT DOCUMENTS

| 1,134,720 | A |  | 4/1915 | Bradley |
| 3,608,103 | A |  | 9/1971 | Seid |
| 3,694,831 | A |  | 10/1972 | Treace |
| 3,808,615 | A |  | 5/1974 | Geary |
| 3,874,010 | A |  | 4/1975 | Geary |
| 4,074,374 | A |  | 2/1978 | Ayesh |
| 4,730,801 | A | * | 3/1988 | Cloward ............... 248/118 |
| 5,054,142 | A |  | 10/1991 | Owens |
| 5,214,814 | A | * | 6/1993 | Eremita et al. ........... 5/636 |
| 5,362,302 | A |  | 11/1994 | Jensen et al. |
| 5,408,713 | A |  | 4/1995 | Stratton et al. |
| 5,410,769 | A | * | 5/1995 | Waterman .............. 5/632 |
| 5,423,861 | A |  | 6/1995 | Kelley |
| 5,466,039 | A |  | 11/1995 | Umbrianna |
| 5,537,702 | A | * | 7/1996 | Brown-Milants et al. ...... 5/632 |

(Continued)

FOREIGN PATENT DOCUMENTS

EP 0 660 694 B1 11/1997
WO WO 01/49223 A1 7/2001

OTHER PUBLICATIONS

EarthGear™ therapeutic innovations, Pinnacle, www.earthgear.com, 1 pg.

(Continued)

*Primary Examiner*—Alexander Grosz
(74) *Attorney, Agent, or Firm*—Dean D. Small; The Small Patent Law Group

(57) ABSTRACT

Methods and systems for medical imaging using an ergonomic patient head an arm support are provided. A support for medical imaging is provided that includes a lower body configured to engage a portion of a medical imaging system and an upper surface having a plurality of depressions configured to receive therein at least one of a head and arm of a patient.

19 Claims, 11 Drawing Sheets

U.S. PATENT DOCUMENTS

| | | | |
|---|---|---|---|
| 5,661,860 A | 9/1997 | Heitz | |
| 5,678,266 A | 10/1997 | Petringa et al. | |
| 5,771,512 A * | 6/1998 | Kurakake et al. | 5/623 |
| 5,782,244 A * | 7/1998 | Kostich | 128/869 |
| 5,893,183 A | 4/1999 | Bechtold | |
| 6,684,431 B2 | 2/2004 | Splane, Jr. | |
| 6,718,581 B2 | 4/2004 | Riach | |
| 6,758,447 B2 | 7/2004 | Tinsley | |
| 2002/0100846 A1 | 8/2002 | Tinsley | |
| 2002/0184706 A1 | 12/2002 | Riach | |
| 2003/0084512 A1* | 5/2003 | Fujita et al. | 5/601 |
| 2003/0084513 A1 | 5/2003 | Splane, Jr. | |
| 2005/0066444 A1* | 3/2005 | Mazzei et al. | 5/638 |
| 2007/0053502 A1 | 3/2007 | Zelnik et al. | |
| 2008/0005840 A1 | 1/2008 | Zelnik | |
| 2008/0005841 A1 | 1/2008 | Zelnik et al. | |

OTHER PUBLICATIONS

Sinmed Radiotherapy producats, Sinmed Poly-ehtylene cushions, www.sinmed.nl, copyright 2003, 1pg.
Siemens medical, e.cam Signature Series Manual, 8 pgs.
cfi Medical Solutions contour fabricators, inc. Manual, 45 pgs.
Oakworks® Medical Equipment, www.oakworksmed.com, 4 pgs.
Banner Therapy Products, "Prone Pillow Pad", www.bannertherapy.com, 2 pgs.
Banner Therapy Products, "Prone Pillow by Chatt", www.bannertherapy.com, 2 pgs.
Banner Therapy Products, "Prone Pillow—MaxRelax", www.bannertherapy.com, 2 pgs.
Sinmed Radiotherapy products, "Posirest", www.sinmed.nl, 2 pgs.
Nuclear Medicine Instruments & Accessories, Catalog 28, Pinestar Technology, Inc. 134 pgs.

\* cited by examiner

METHODS AND APPARATUS FOR ERGONOMIC ARM AND HEAD SUPPORT

CROSS REFERENCE TO RELATED APPLICATIONS

This application claims priority to and the benefit of the filing date of U.S. Provisional Application No. 60/710,709, filed on Aug. 23, 2005, entitled "METHODS AND APPARATUS FOR ERGONOMIC ARM AND HEAD SUPPORT," which is hereby incorporated by reference in its entirety.

BACKGROUND OF THE INVENTION

This invention relates generally to medical imaging systems and, more particularly, to devices that ergonomically maintain a stable patient position in medical imaging systems.

Nuclear cardiology scanning requires the patient to lie with his or her arms above his or her head so as to leave the torso clear for scanning and allow the detectors to get as close as possible to the heart. Holding this unnatural position for a long scanning time, for example, fifteen minutes or more, is difficult to impossible for most patients, in particular older patients with stiffness in the shoulder joint. Further, patients often have difficulty lowering the arms after the completion of the scan and suffer pain for several hours after scanning. Additionally, the positioning of a patient's legs during such scanning also is often uncomfortable and can, for example, place stress on a patient's back.

BRIEF DESCRIPTION OF THE INVENTION

In one embodiment, a support for medical imaging is provided that includes a lower body configured to engage a portion of a medical imaging system and an upper surface having a plurality of depressions configured to receive therein at least one of a head and arm of a patient.

In another embodiment, a support for medical imaging is provided that includes an upper portion having an opening for receiving therein a face of a patient and configured to support a head of the patient above a table of the medical imaging system. The support further includes a lower portion having a shoulder portion configured to support arms of the patient below the table of the medical imaging system.

In yet another embodiment, a leg support for medical imaging is provided that includes a first portion defining part of a curved body and a second portion defining part of the curved body. The first portion is longer than the second portion and the curved body is configured to engage a patient table of a medical imaging system to support legs of a patient in one of a prone and supine position.

DETAILED DESCRIPTION OF THE INVENTION

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Figure 1:
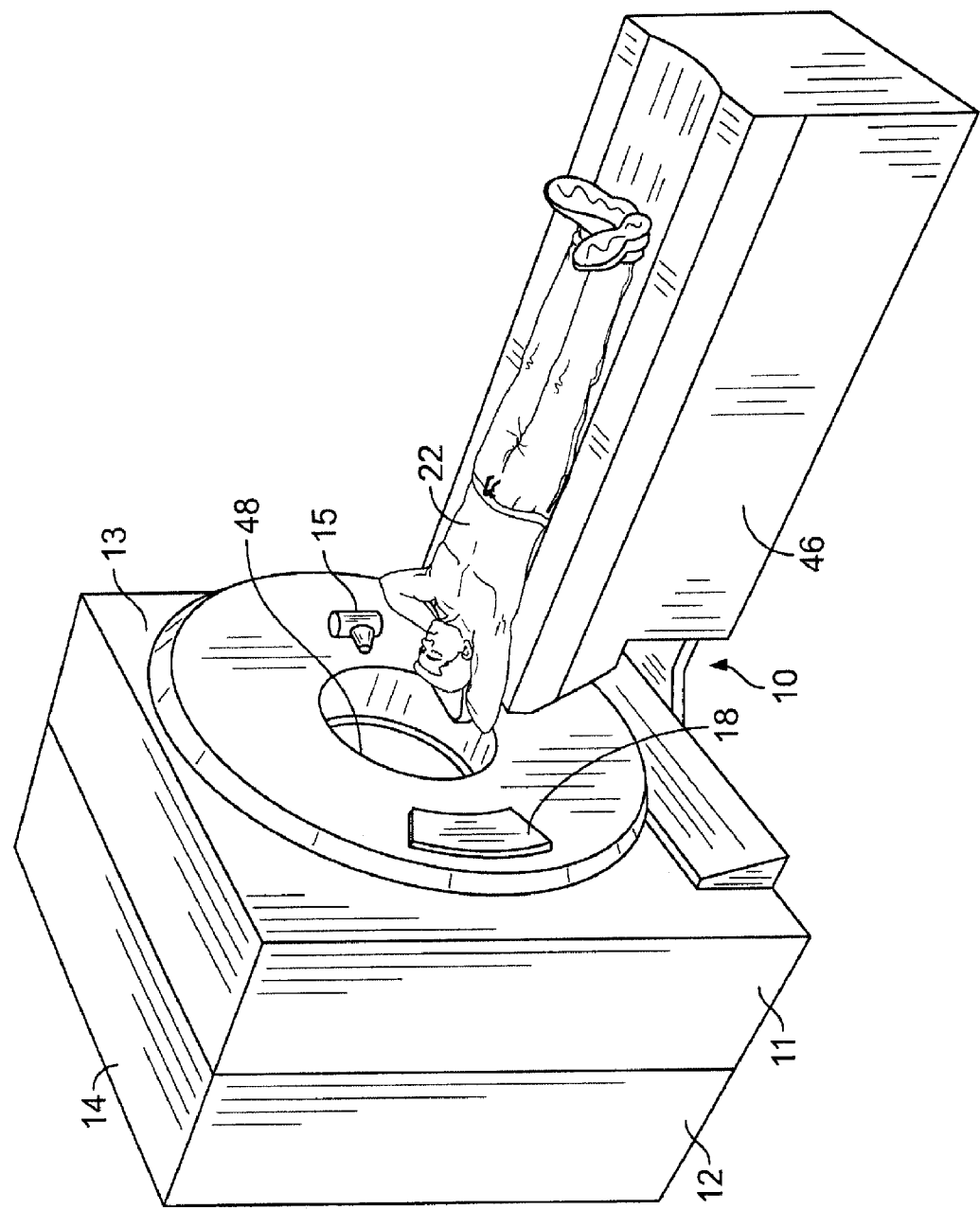
FIG. 1 is a perspective view of an exemplary imaging system.
Figure 2:
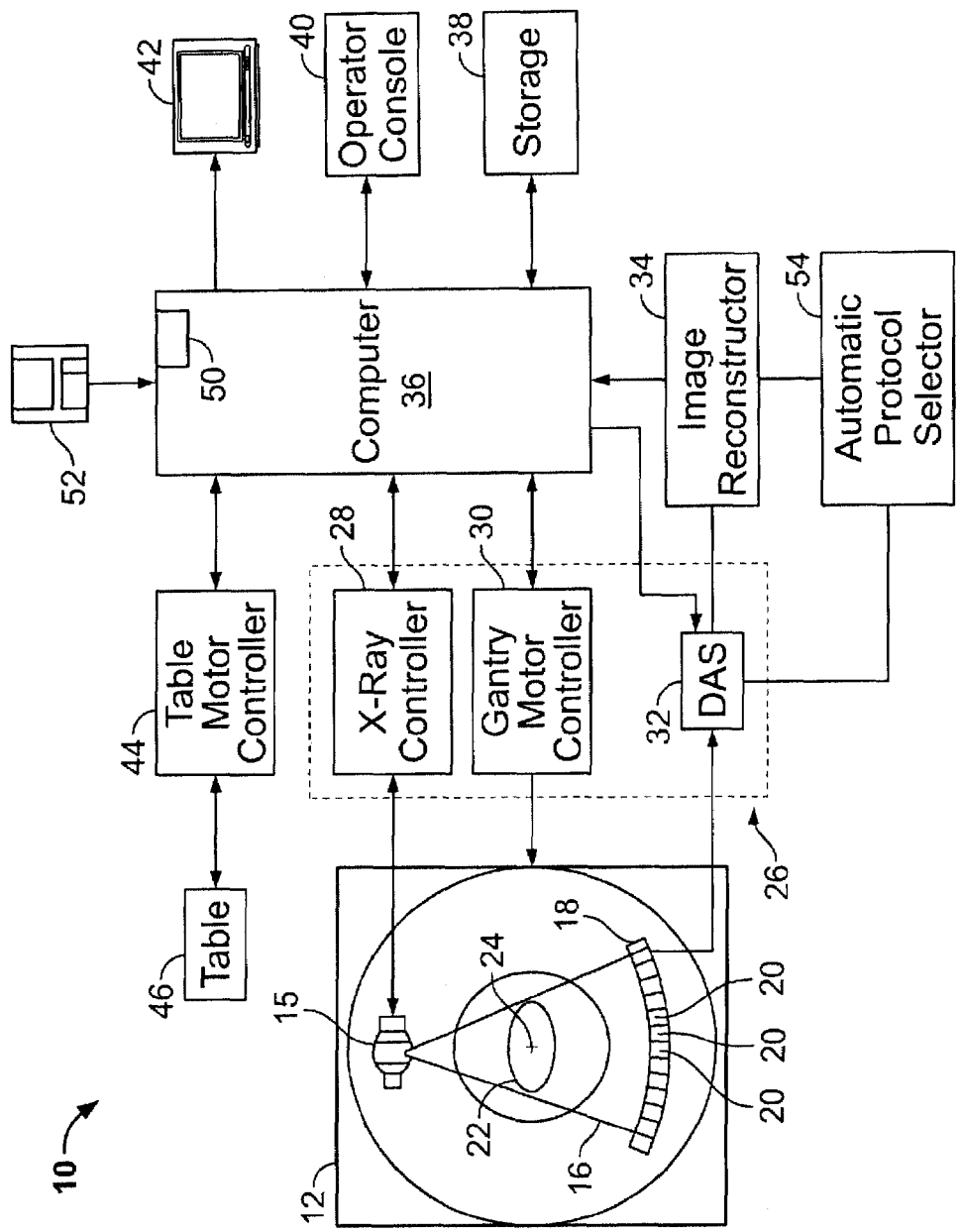
FIG. 2 is a schematic block diagram of the imaging system shown in FIG. 1.

FIG. 1 is a perspective view of an exemplary imaging system 10 constructed in accordance with various embodiments of the invention. FIG. 2 is a schematic block diagram of the imaging system 10 (shown in FIG. 1). In the exemplary embodiment, the imaging system 10 is a multi-modal imaging system and includes a first modality unit 11 and a second modality unit 12. The modality units 11 and 12 enable the system 10 to scan an object, for example, a patient, in a first modality using the first modality unit 11 and to scan the object in a second modality using the second modality unit 12. The system 10 allows for multiple scans in different modalities to facilitate an increased diagnostic capability over single modality systems. In one embodiment, the multi-modal imaging system 10 is a Computed Tomography/Positron Emission Tomography (CT/PET) imaging system 10. The CT/PET system 10 includes a first gantry 13 associated with the first modality unit 11 and a second gantry 14 associated with the second modality unit 12. In alternative embodiments, modalities other than CT and PET may be employed with the imaging system 10. The gantry 13, in an embodiment, includes the first modality unit 11 that has an x-ray source 15 that projects a beam of x-rays 16 toward a detector array 18 on the opposite side of the gantry 13. The detector array 18 is formed by a plurality of detector rows (not shown) including a plurality of detector elements 20 that together sense the projected x-rays that pass through an object, such as a patient 22. Each detector element 20 produces an electrical signal that represents the intensity of an impinging x-ray beam and allows estimation of the attenuation of the beam as the beam passes through the object or patient 22.

In other embodiments, the system 10 includes only a single gantry having a first rotor configured to carry the first modality system and a second rotor configured to carry the second modality system. In various other embodiments the system 10 includes only one modality, such as CT.

During a scan to acquire x-ray projection data the gantry 13 and the components mounted thereon rotate about an examination axis 24. FIG. 2 shows only a single row of detector elements 20 (i.e., a detector row). However, the detector array 18 may be configured as a multislice detector array having a plurality of parallel detector rows of detector elements 20 such that projection data corresponding to a plurality of slices can be acquired simultaneously during a scan. To acquire emission data, the gantry 14 rotates one or more gamma cameras (not shown) about the examination axis 24. The gantry 14 may be configured for continuous rotation during an imaging scan and/or for intermittent rotation between imaging frames.

The rotation of the gantries 13 and 14, and the operation of the x-ray source 15 are controlled by a control mechanism 26 of the system 10 (e.g., CT/PET system). The control mechanism 26 includes an x-ray controller 28 that provides power and timing signals to the x-ray source 15 and a gantry motor controller 30 that controls the rotational speed and position of the gantry 13 and the gantry 14. A data acquisition system (DAS) 32 of the control mechanism 26 samples data from the detector elements 20 and the gamma cameras and conditions the data for subsequent processing. An image reconstructor 34 receives sampled and digitized x-ray data and emission data from the DAS 32 and performs high-speed image reconstruction. The reconstructed image is transmitted as an input to a computer 36 that stores the image in a storage device 38.

The computer 36 also receives commands and scanning parameters from an operator via console 40 that has an input device, such as, a keyboard. An associated display 42 allows the operator to observe the reconstructed image and other data from the computer 36. Operator supplied commands and parameters are used by the computer 36 to provide control signals and information to the DAS 32, the x-ray controller 28 and the gantry motor controller 30. In addition, the computer 36 operates a table motor controller 44 that controls a motorized table 46 to position the patient 22 in the gantry 13 and 14. Specifically, the table 46 moves portions of the patient 22 through the gantry opening 48.

In one embodiment, the computer 36 includes a read/write device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, the computer 36 executes instructions stored in firmware (not shown). The computer 36 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. The system 10 may also includes a plurality of other detectors, for example, PET detectors (not shown) including a plurality of detector elements. The PET detectors and the detector array 18 both detect radiation and are both referred to herein as radiation detectors.

An automatic protocol selector 54 is communicatively coupled to the DAS 32 and the image reconstructor 34 to transmit settings and parameters for use by the DAS 32 and the image reconstructor 34 during a scan and/or image reconstruction and image review. Although the automatic protocol selector 54 is illustrated as a separate component, it should be understood that that functions performed by the automatic protocol selector 54 may be incorporated into functions performed by, for example the computer 36. Accordingly, the automatic protocol selector 54 may be embodied in a software code segment executing on a multifunctional processor or may embodied in a combination of hardware and software.

Additionally, although described in a medical setting, it is contemplated that the embodiments of the invention may be implemented in connection with other imaging systems including industrial CT systems such as, for example, but not limited to, a baggage scanning CT system typically used in a transportation center such as, for example, but not limited to, an airport or a rail station, non-destructive testing systems, etc.

Figure 3:
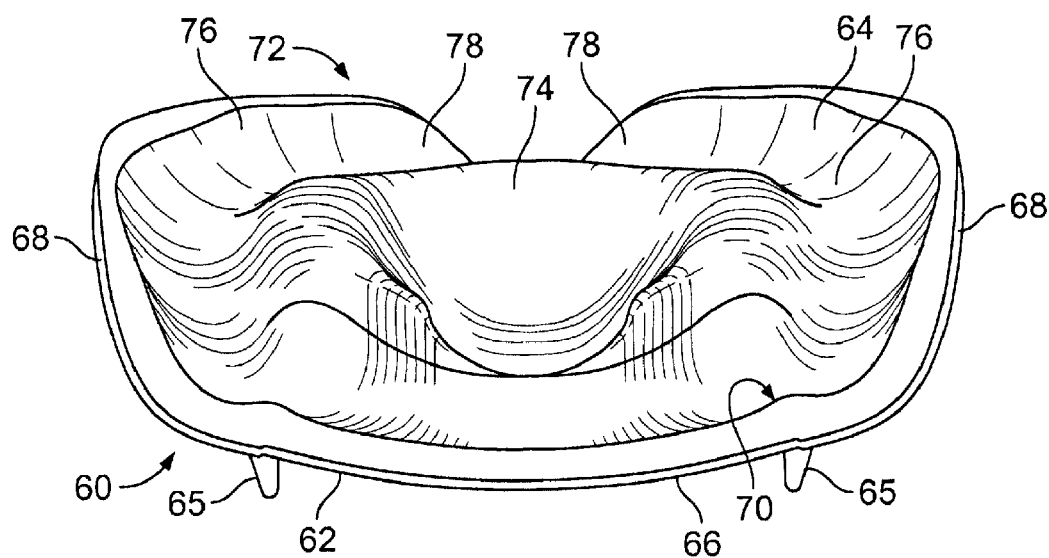
FIG. 3 is a perspective view of an exemplary ergonomically shaped head and arm support constructed in accordance with an embodiment of the invention.

FIG. 3 is a perspective view of an exemplary ergonomically shaped head and arm support 60 that may be used with the system 10 shown in FIG. 1. In the exemplary embodiment, the head and arm support 60 includes a lower body 62 and a cushion portion 64 within the lower body portion and configured to receive at least one of a patient's head, upper arms, forearms, and hands therein. The lower body 62 includes engagement members, for example, at least one leg 65 extending vertically downward from the lower body 62. The at least one leg 65 is configured to mate with a complementary portion, for example, a complementary slot or hole positioned in a movable patient table surface 100 (shown in FIG. 5) of an imaging system 110 (shown in FIG. 5). The lower body 62 includes a base portion 66, which in one embodiment is substantially planar and in an alternate embodiment is slightly curved. Sidewalls 68 extend vertically upward around an outer periphery of the cushion portion 64. In the exemplary embodiment, the sidewalls 68 extend around three sides of the cushion portion 64 such that an opening is formed on one end, for example, proximate a patient table surface. A lower surface 70 of the cushion portion 64 is configured to substantially mate with the lower body 62 and the three sides of the sidewalls 68. Further, it should be noted that the lower body 62 is shaped to extend increasingly outwardly from the base portion 66 vertically upward along the sidewalls 68.

An upper surface 72 of the cushion portion 64 includes a first depression 74 defining a first recessed portion or indentation configured to receive a patient head. Second depressions 76 define second recessed portions or indentations configured to receive a patient's arms. Third depressions 78 define third recessed portions or indentations configured to receive a patient's hands. In the various embodiments, the lower body 62 is fabricated from a structurally rigid or semi-rigid material, for example, plastic. The cushion portion 64 is fabricated from a foam material, which is typically covered in plastic or textile material. In one exemplary embodiment, the lower body 62 is fabricated from an ethylene material and the cushion portion 64 is fabricated from a viscoelastic material.

The lower body 62 is formed as a single molded piece, for example, a single unitary piece. The cushion portion 64 may be formed of one or more cushion pieces covered in, for example, fabric covers satisfying medical standards for use.

Figure 4:
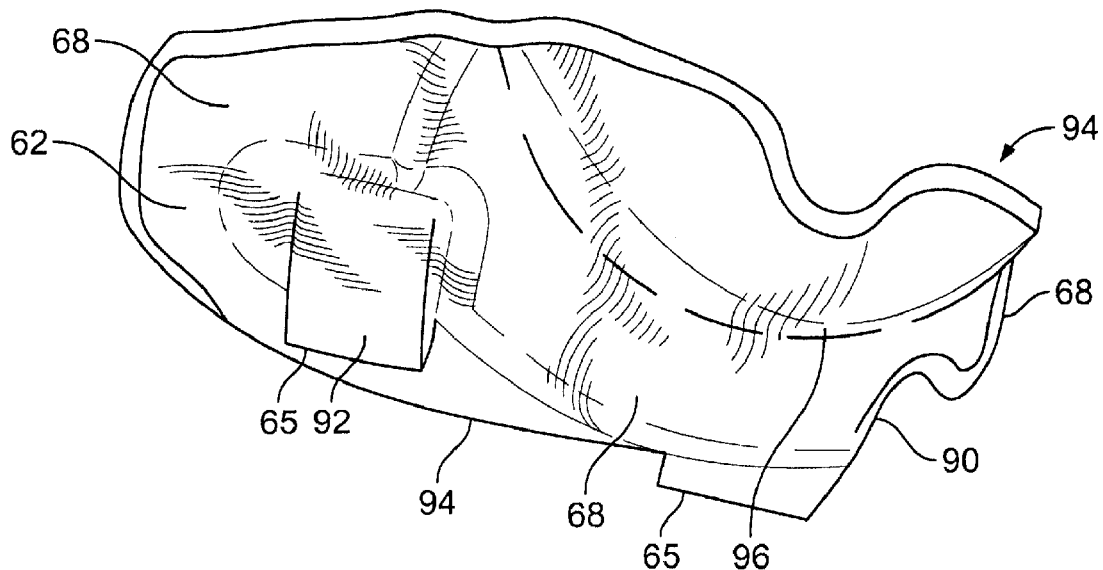
FIG. 4 is a lower perspective view of the ergonomically shaped head and arm support shown in FIG. 3.

FIG. 4 is a lower view of the head and arm support 60 shown in FIG. 3. A lower surface 90 of the lower body 62 includes the at least one leg 65 extending vertically downward from the lower body 62. The at least one leg 65 is configured to engage a patient table as described herein. The at least one leg 65 facilitates preventing movement of the head and arm support 60 with respect to the patient table during a scan. In an exemplary embodiment, two legs 65 are provided on opposite sides of the lower body 62. Each leg has a generally planar surface 92 that extends generally vertically upward along a corresponding sidewall 68. The pair of sidewalls 68 are on opposite sides of the lower body 62. Each leg 65 is recessed within the corresponding sidewall 68 and extends beyond a lower surface 94 of the base portion 66. The lower body 62 also includes at an upper end 94 an engagement portion 96 configured to engage a bore 102 of the imaging system 110 (both shown in FIG. 5). The engagement portion 96 is configured in one embodiment as an arcuately shaped region (e.g., a step or semi-circular region) dimensionally configured to engage the bore 102.

Figure 5:
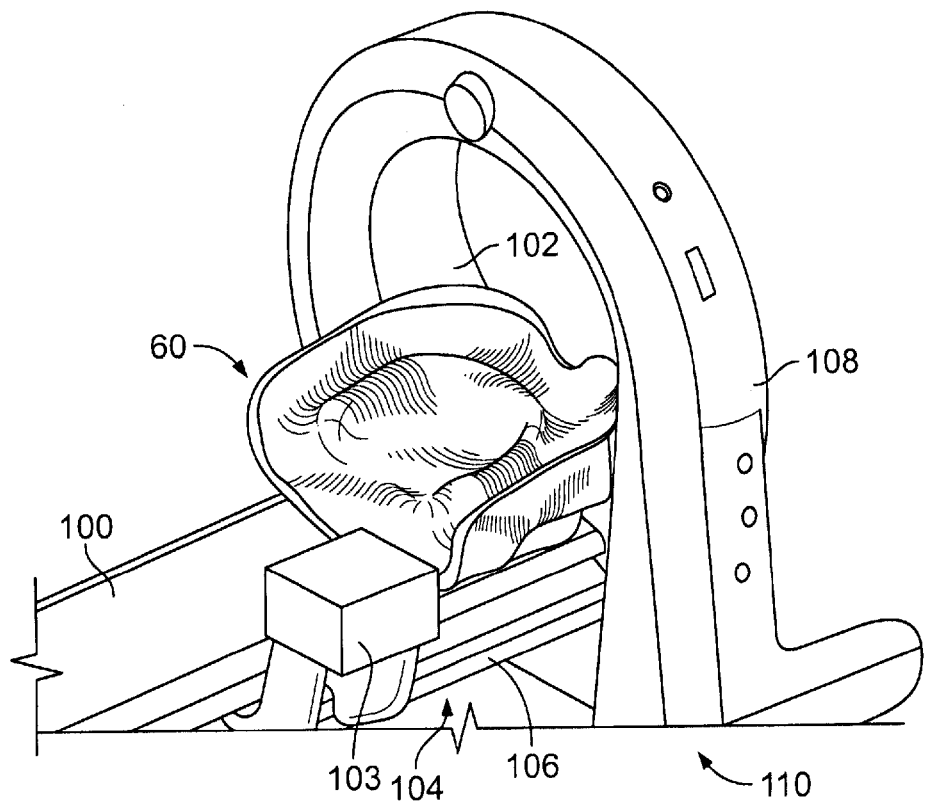
FIG. 5 is a perspective view of the ergonomically shaped head and arm support of FIG. 3 coupled to a patient table.

FIG. 5 is a perspective view of the head and arm support 60 coupled to the movable patient table surface 100 of the imaging system 110 (e.g., CT imaging system). The movable patient table surface 100 may be provided as part of a motorized table 104 that includes a stationary table frame 106. A gantry 108, for example, a single gantry is provided and includes a plurality of detector elements (not shown). The gantry 108 includes the bore 102 therethrough. The movable patient table surface 100 is supported on the stationary table frame 106 and may include movable members (e.g., wheels or slides) configured to allow movement of the movable patient table surface 100, for example, laterally in and out of the gantry 108. It should be noted that the stationary table frame 106 also may be configured to provide upward and downward movement of the movable patient table surface 100.

The head and arm support 60 is configured to couple to the movable patient table surface 100 such that a patient reclining in the supine position on the movable patient table surface 100 can access the indentations within the cushion portion 64 to support the patient's head, arms and/or legs. More particularly, the legs 65 (shown in FIGS. 3 and 4) are configured to engage within, for example, slots of the movable patient table surface 100 or a palette connected thereto. Additionally, the engagement portion 96 (shown in FIG. 4) is configured to abut and engage within the bore 102.

It should be noted that additional components may be provided in connection with the imaging system 110. For example, an electrocardiogram (ECG) monitor 103 may be provided in connection with a portion of the movable patient table surface 100 or mounted to the stationary table frame 106.

Figure 6:
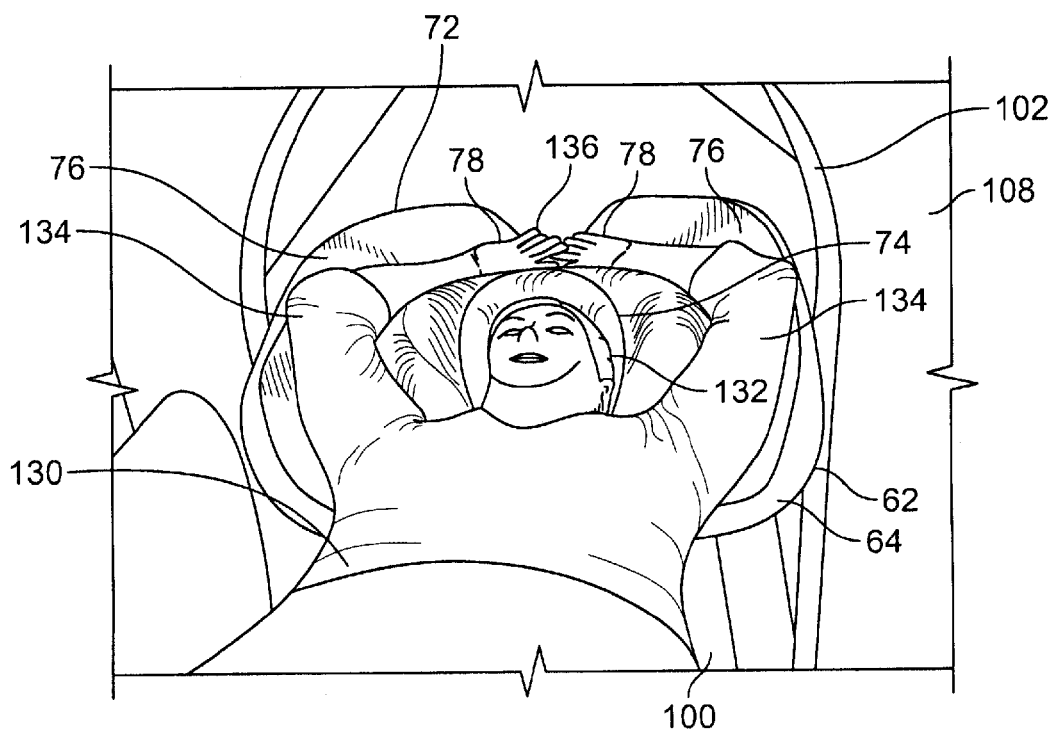
FIG. 6 is a perspective axial view of the system shown in FIG. 1 having the ergonomically shaped head and arm support connected thereto.

FIG. 6 is a perspective axial view of an imaging system, for example, the imaging system 110 (shown in FIG. 5) or the imaging system 10 (shown in FIG. 1). In the exemplary embodiment, a patient 130 is reclining in the supine position on the movable patient table surface 100. The head and arm support 60 is coupled to movable patient table surface 100 such that the patient 130 is able to recline on the movable patient table surface 100 with the patient head 132, arms 134 and hands 136 received in the indentations in the cushion portion 64. Specifically, the patient head 132 is received within the first depression 74, the patient's arms 134 received within the second depressions 76 and the patient's hands 78 received within the third depressions 78.

The head and arm support 60 is configured to accommodate and fit the dimensions of a wide range of patients, for example, during long duration supine scans with the arms 134 raised above the head 132. The first depression 74 facilitates fixing the patient head in place and providing reproducibility of patient positioning and the angled lower body 62 forms second depressions 76 that accommodate different size arms.

Figure 7:
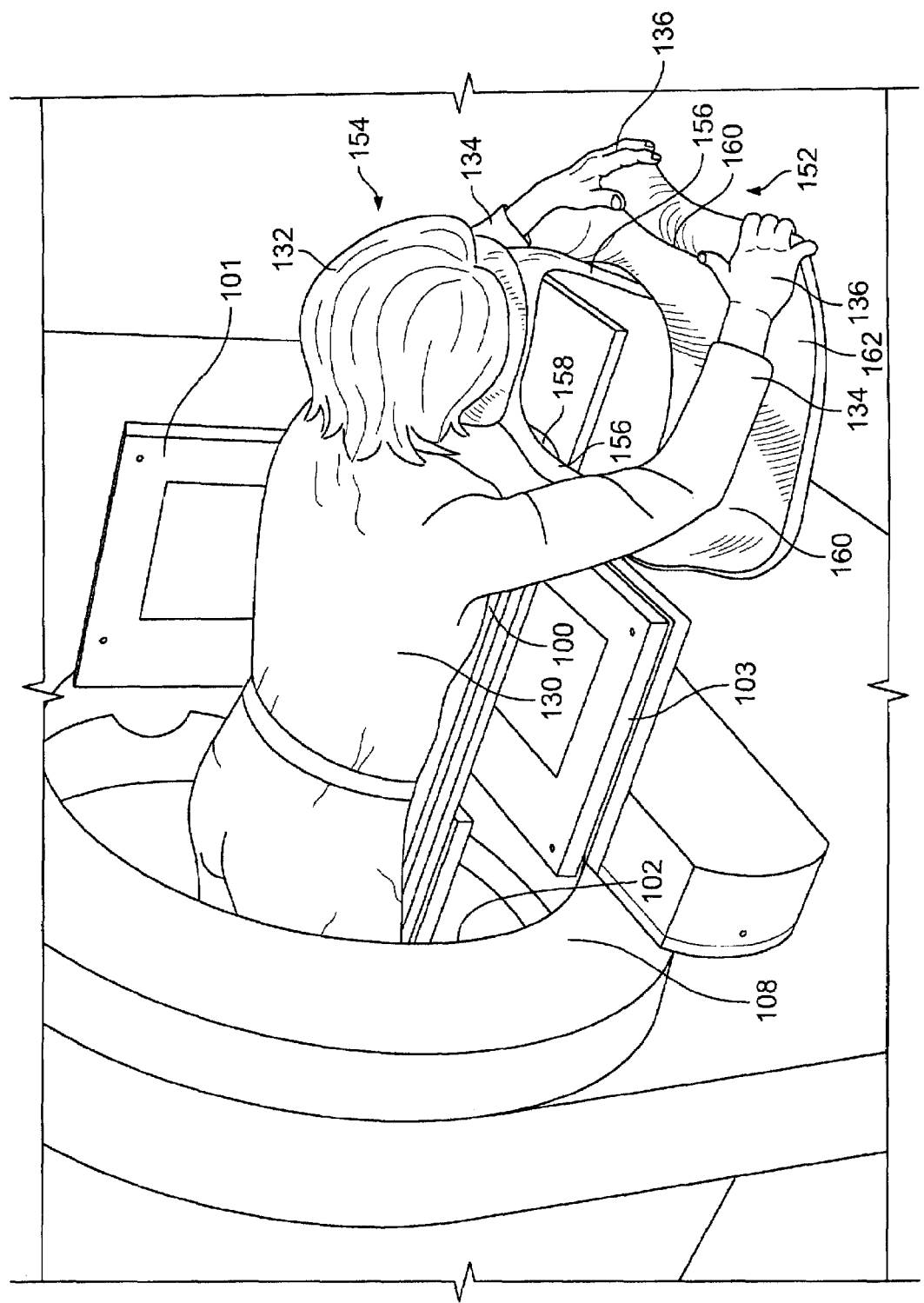
FIG. 7 is a top perspective view of an exemplary ergonomically shaped head and arm support constructed in accordance with another embodiment of the invention.
Figure 8:
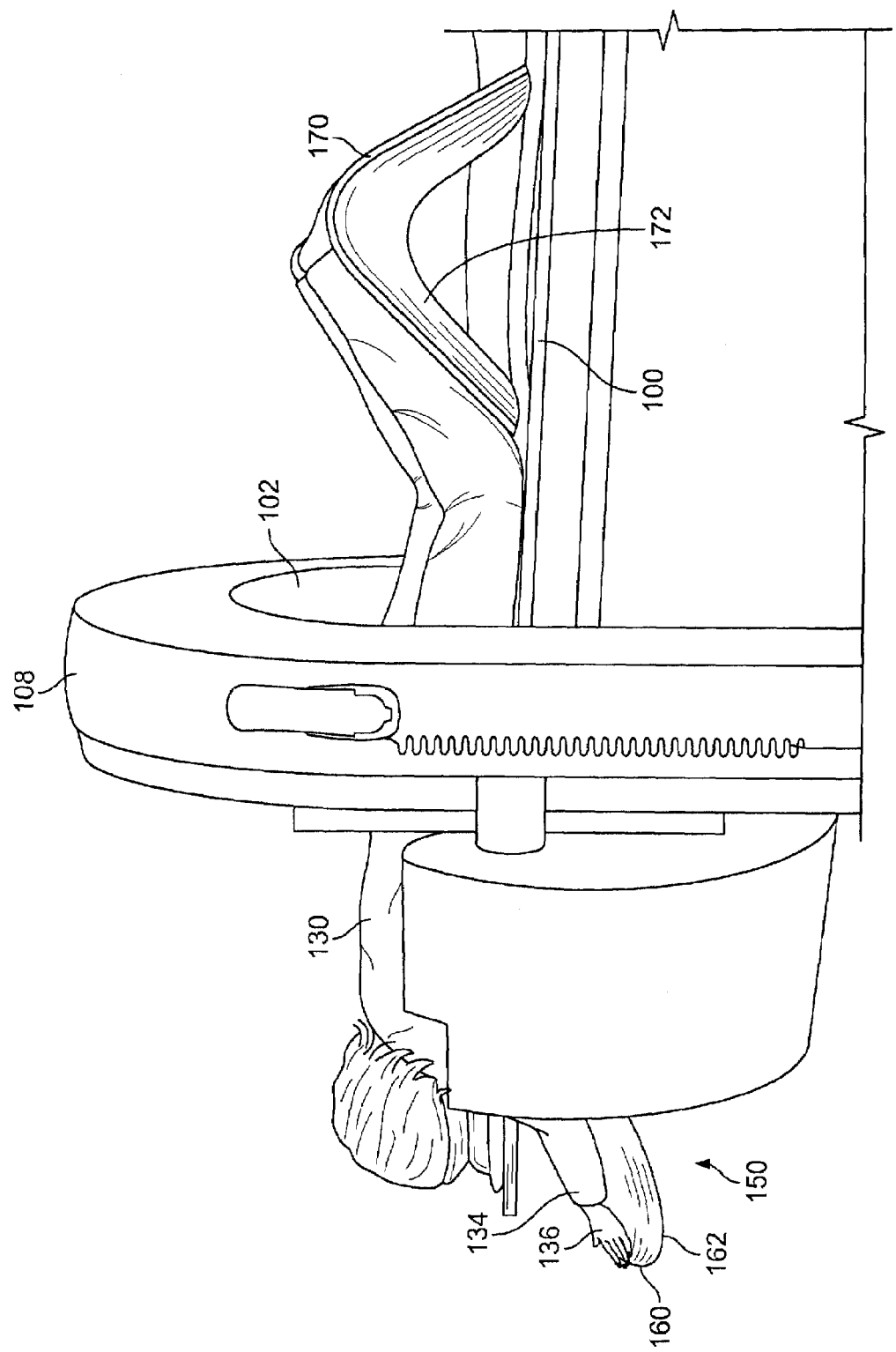
FIG. 8 is a side perspective view of the ergonomically shaped head and arm support shown in FIG. 7.

Various embodiments of the invention also include a head and arm support 150 as shown in FIGS. 7 and 8 configured to support a patient's head 132, arms 134 and hands 136 when positioned in a prone position on the movable patient table surface 100. In this embodiment, the head and arm support 150 includes a lower portion 152 for supporting the arms 134 and hands 136 and an upper portion 154 for supporting the head 132. The upper portion 154 includes an opening therethrough (covered by the patient head in FIGS. 7 and 8) for receiving the face of the patient 130. The upper portion 154 is connected to the lower portion 152 by a plurality of extensions 156 (e.g., legs). The upper portion 154 includes at least one protrusion 158 positioned between where the extensions 156 extend from the upper portion 154. The protrusion 158 is shaped to support the upper portion 154 above and on the movable patient table surface 100 allowing a patient head to be supported above the movable patient table surface 100. The lower portion 152 includes a lower shoulder portion 160 extending around a lower end 162 of the lower portion 152 and configured to support the arms 134 and hands 136 of the patient 130 below the movable patient table surface 100 and parallel to, for example, the floor. This configuration provides an angle of about ninety degrees between a shoulder and upper arm of a patient. The head and arm support 150 is constructed in the various embodiments having a hard shell base (e.g., ethylene base) with a soft material provided on surfaces that may contact a patient (e.g., head contact, face contact, arm contact, etc.) and that may be provided as one or more cushions. For example, a soft cushion material, such as an viscoelastic material or a foam material covered in a fabric may be provided on the patient contact surfaces, or alternatively, along the entire top and side surfaces of the head and arm support 150.

It should be noted that the head and arm support 150 as shown in FIGS. 7 and 8 may be used in connection with different types of imaging systems. As shown, the imaging system is a nuclear medicine (NM) imaging scanner having a first detector head 101 (e.g., a first gamma camera) and a second detector head 103 (e.g., a second gamma camera). Although shown in an L-mode configuration wherein the first detector head 101 is perpendicular to the second detector head 103, other configuration are contemplated, for example, an H-mode configuration wherein the first detector head 101 is parallel to and opposing the second detector head 103 with a patient therebetween. In the embodiment shown the second detector head 103 is positioned parallel to and below the movable patient table surface 100. Accordingly, the material used for the movable patient table surface 100 and any padding on the movable patient table surface 100 allow for detection through the movable patient table surface 100 by the second detector head 103.

Figure 9:
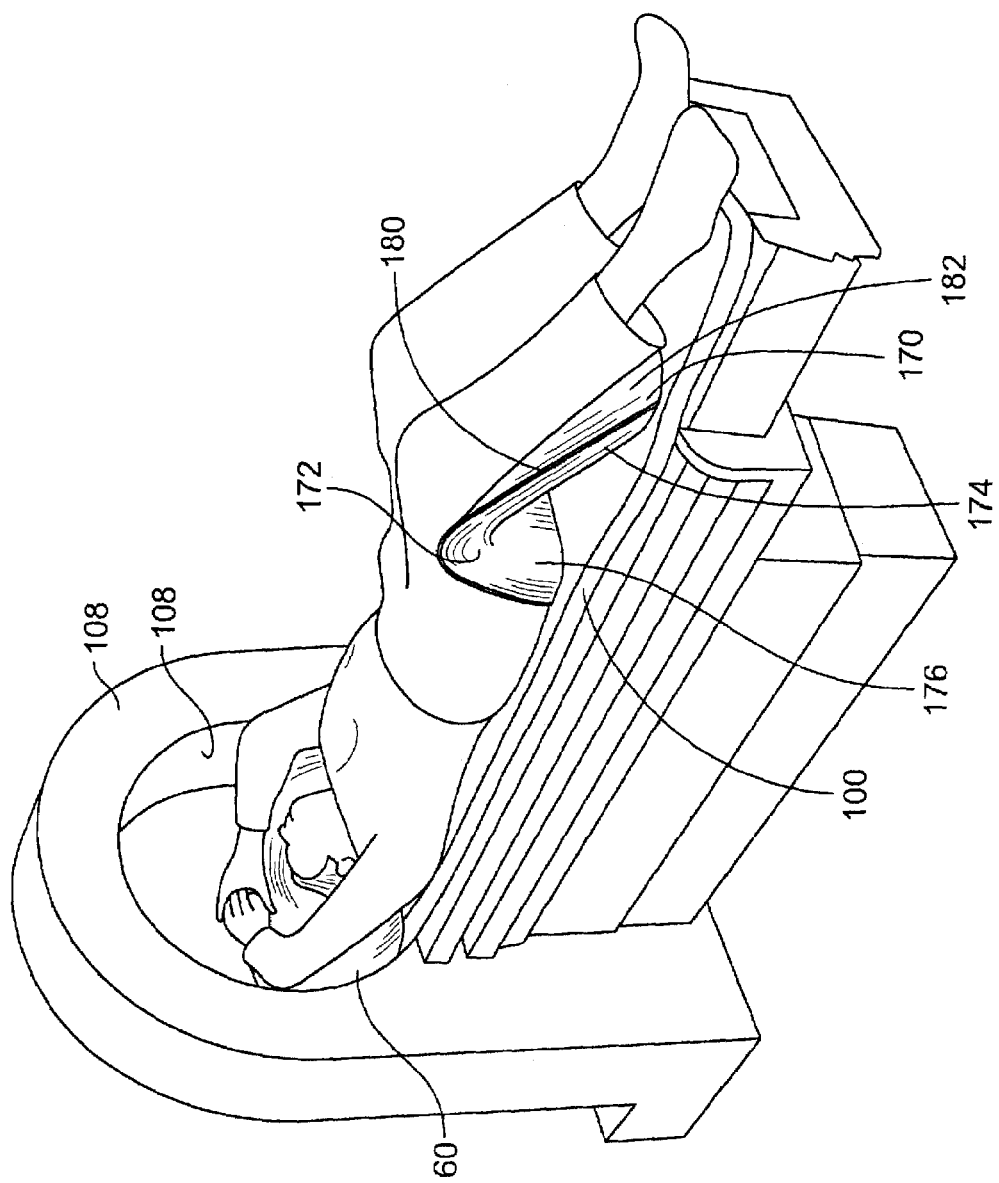
FIG. 9 is a top perspective view of an exemplary ergonomically shaped head and arm support and an ergonomically shaped leg support constructed in accordance with another embodiment of the invention.
Figure 10:
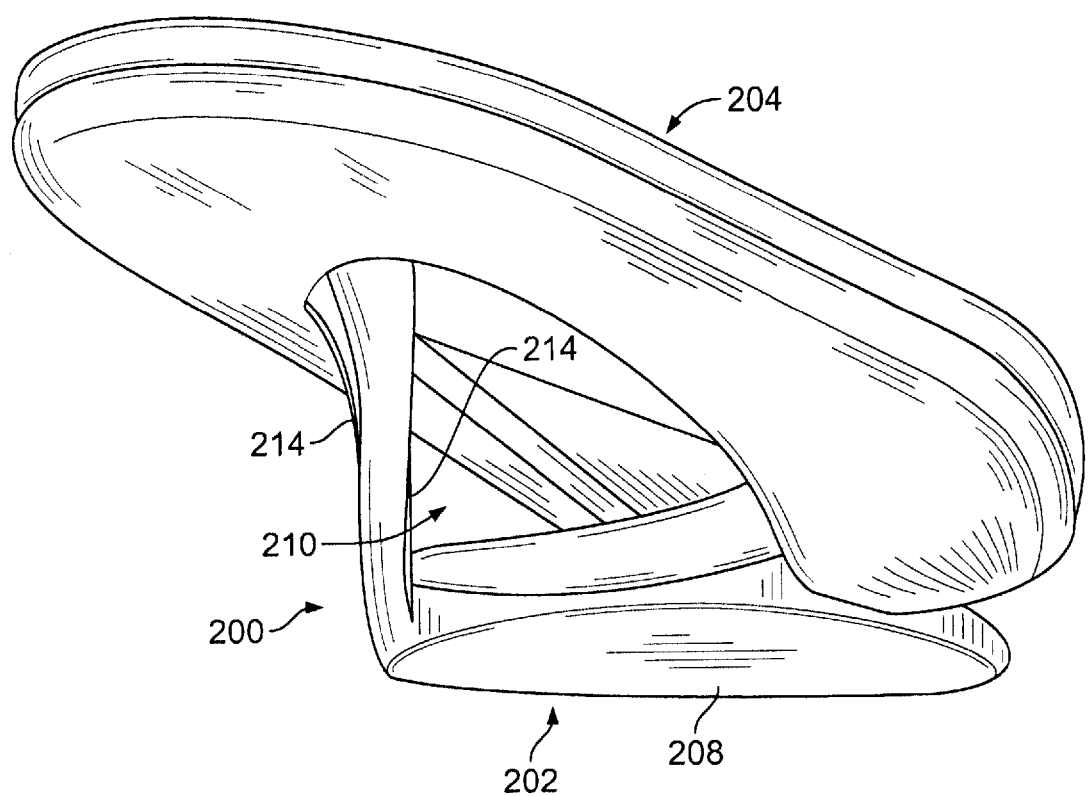
FIG. 10 is a side perspective view of an exemplary ergonomically shaped head and arm support constructed in accordance with another embodiment of the invention.
Figure 11:
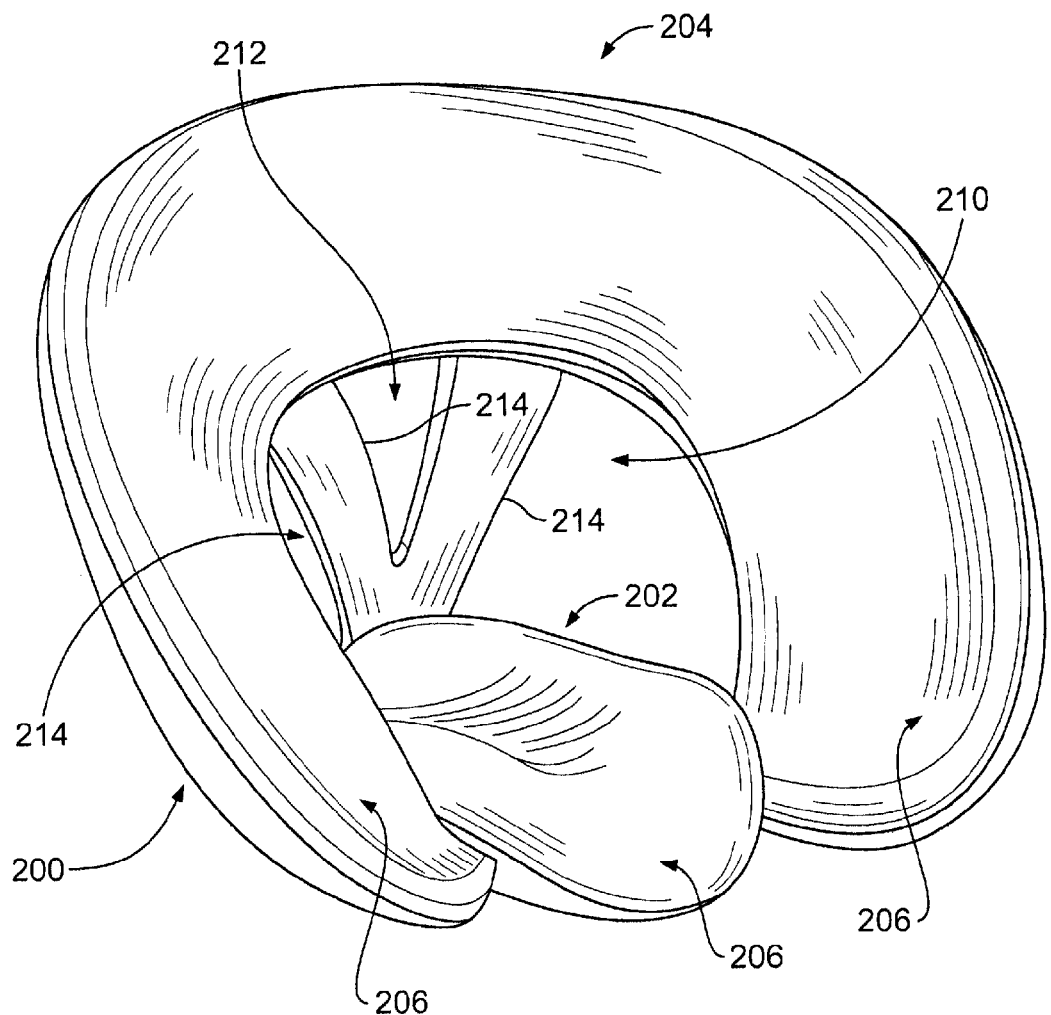
FIG. 11 is a top perspective view of the ergonomically shaped head and arm support shown in FIG. 10.
Figure 12:
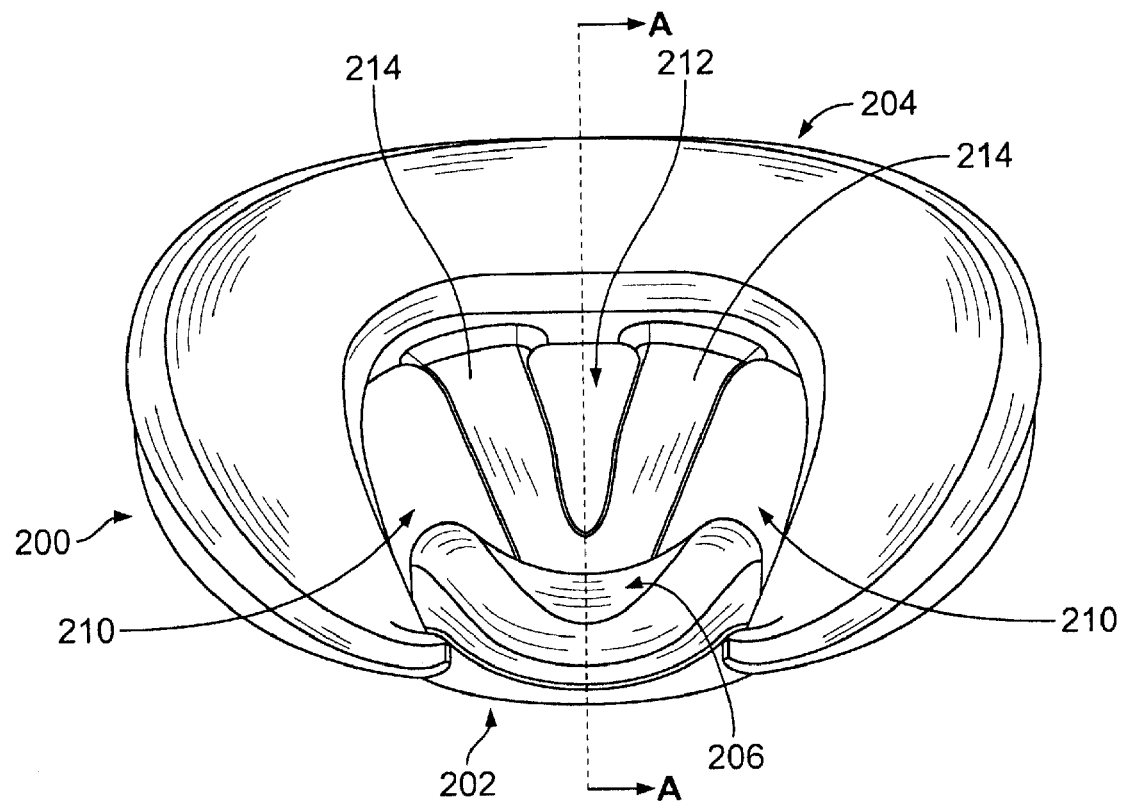
FIG. 12 is a front elevation view of the ergonomically shaped head and arm support shown in FIG. 10.
Figure 13:
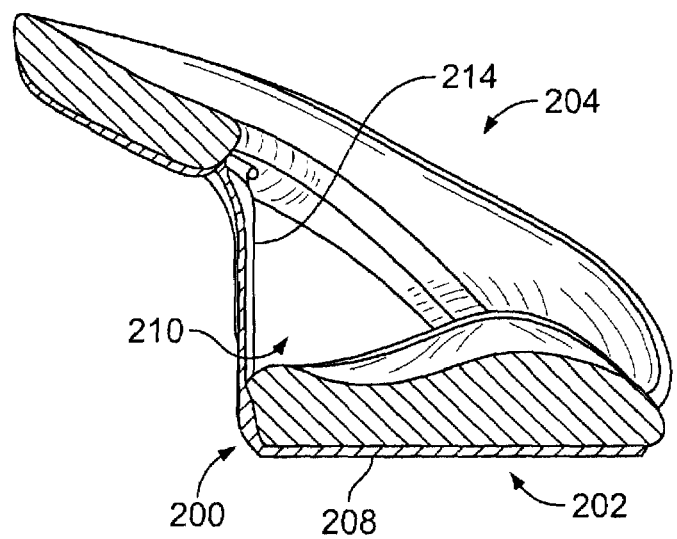
FIG. 13 is a side elevation view of the ergonomically shaped head and arm support shown in FIG. 10.
Figure 14:
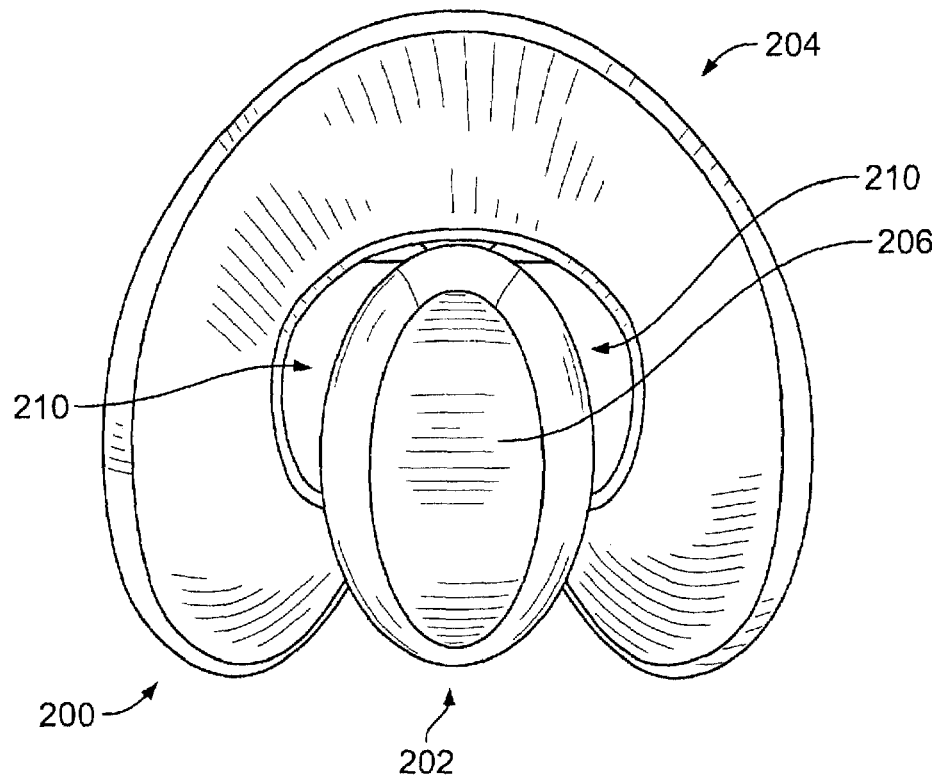
FIG. 14 is a top plan view of the ergonomically shaped head and arm support shown in FIG. 10.

Additionally, as shown in FIGS. 8 and 9, a leg support 170 may be provided that includes a generally curved body 172 that may be "U" shaped and/or "J" shaped. For example, a first portion 174 of the body 172 may be longer than a second portion 176 of the body 172 as shown in FIG. 9. This allows support of the legs in both the supine and prone position, for example, when the leg support 170 is rotated (shown in different positions in FIGS. 8 and 9). Further, in various embodiments, sides 180 extending longitudinally along an edge of the leg support 170 are raised, for example, to allow a patient to relax and prevent legs of the patient from falling off the leg support 170 when knees of the patient are open. The body 172 may be formed of a rigid base, such as, from a hard shell fabricated of ethylene with a cushion layer 182 (e.g., a viscoelastic material) on a top surface of the leg support 170. Additionally, a fabric may be provided to cover the cushion layer 182. However, the head and arm support 150 and the leg support 170 may be fabricated of any suitable material, for example, any type of plastic with a soft or foam type material on top.

The leg support 170 may be modified, for example, markings may be added to the top surface or at one of the ends to identify a position, such as a desirable position, of a patient's feet for supine imaging.

Although various embodiments are described above with respect to medical imaging, for example, a nuclear medicine system, other medical imaging modalities, such as computed tomography (CT), single positron emission tomography (SPECT), positron emission tomography (PET), nuclear magnetic resonance imaging (MRI), static X-ray imaging, dynamic (Fluoroscopy) X-ray imaging, and multimodality combinations thereof may also benefit form the methods described herein and the use of the present invention is contemplated with respect to these modalities. Further, the various embodiments may be implemented in connection with non-medical imaging systems.

The above-described embodiments of a medical imaging system provide a cost-effective and reliable means for fixing a patient position during a relatively long duration scan in a comfortable and reproducible orientation. The support is configured to provide ergonomic and comfort features to ease the anxiety of patients.

Exemplary embodiments of medical imaging systems and apparatus are described above in detail. The medical imaging system components illustrated are not limited to the specific embodiments described herein, but rather, components of each system may be utilized independently and separately from other components described herein. For example, the medical imaging system components described above may also be used in combination with different medical imaging system components.

Additionally, the various support members may be modified or configured differently. For example, the head and arm support 60 shown in FIGS. 3 through 6 may be modified as shown in FIGS. 10 through 14. In particular, a head and arm support 200 may be provided similar to the head and arm support 60. In this embodiment, a lower portion 202 configured to support a patient's head and an upper portion 204 configured to support a patient's arms and hands. Each of the lower portion 202 and upper portion 204 include depressions 206 similar to those of the head and arm support 60 and configured to receive therein either a patient's head or a patients, arms and hands, respectively. Each of the lower portion 202 and upper portion 204 generally define a shell that include one or more cushion portions thereon or therein similar to the head and arm support 60 and which may be fabricated from a foam material covered in a plastic or textile material. Other materials may be used, for example, the cushion portions may be fabricated from a viscoelastic material. The lower portion 202 and upper portion 204 may be formed from a structurally rigid or semi-rigid material such as plastic. The cushion portions may be provided in area more likely to be contacted by a portion of patient or may encompass (e.g., line) the entire upper surfaces of both the lower portion 202 and upper portion 204.

In this embodiment, the lower portion 202 has a generally planar lower surface 208. Further, side openings 210 are provided between the lower portion 202 and upper portion 204. Also, a back opening 212 is formed between legs 214 extending between the lower portion 202 and upper portion 204. The legs 214 may be slanted inward from the upper portion 204 to the lower portion 202 and generally forming a "V" shape. The legs 214 support upper portion 204 above the lower portion 202 such that the upper end of the upper portion 204 is higher than the lower end of the upper portion 204 to thereby support a patient's arms and hands elevated above a patient's head.

A technical effect of the various embodiments of the systems and methods described herein include facilitating operation of the medical imaging system by providing patient support and comfort that encourages patient cooperation in maintaining a constant fixed position during a scan.

While the invention has been described in terms of various specific embodiments, those skilled in the art will recognize that the invention can be practiced with modification within the spirit and scope of the claims.

What is claimed is:

1. A support for medical imaging, said support comprising:
   a lower body configured to engage a portion of a medical imaging system; and
   an upper surface extending along the lower body and being shaped to have a plurality of depressions, the plurality of depressions including a first recessed portion shaped to receive a head of a patient and at least one second recessed portion shaped to receive an arm of the patient, wherein the second recessed portion extends from a front end and curves around the first recessed portion such that a hand of the patient is positioned behind the head.

2. A support in accordance with claim 1 further comprising a cushion portion within the lower body.

3. A support in accordance with claim 2 wherein the cushion portion comprises a viscoelastic material.

4. A support in accordance with claim 1 wherein the plurality of depressions comprises at least one recessed portion shaped to receive hands of the patient.

5. A support in accordance with claim 1 wherein the lower body comprises at least one leg for engaging a portion of a table of the medical imaging system.

6. A support in accordance with claim 1 wherein the lower body comprises an engagement portion at an upper end configured to engage a bore of a gantry of the medical imaging system.

7. A support in accordance with claim 1 wherein the lower body comprises an ethylene material.

8. A support in accordance with claim 1 wherein the lower body is configured to be removably engaged to a moving patient table surface of the medical imaging system.

9. A support in accordance with claim 1 wherein the lower body and upper surface are coupled together in a unitary structure.

10. A support in accordance with claim 1 wherein the upper surface is a common surface that includes the plurality of depressions.

11. A support in accordance with claim 1 wherein the lower body includes a front end shaped to engage shoulders of the patient.

12. A support in accordance with claim 11 wherein the lower body includes a plurality of sidewalls, the front end extending between two opposing sidewalls, the first and second recessed portions being located between the opposing sidewalls and below a height of the sidewalls.

13. A support in accordance with claim 1 wherein the at least one second recessed portion includes a pair of second recessed portions, each second recessed portion being shaped to receive an arm.

14. A support in accordance with claim 13 wherein the lower body includes opposing sidewalls where the upper surface extends therebetween, each second recessed portion extending along and being partially defined by a corresponding sidewall.

15. A support in accordance with claim 1 further comprising a cushion portion within the lower body that includes the upper surface, the cushion portion being shaped to include the plurality of depressions.

16. A support for medical imaging, said support comprising:
   a lower body configured to engage a portion of a medical imaging system; and
   an upper surface extending along the lower body and being shaped to have a plurality of depressions, the plurality of depressions including a first recessed portion shaped to receive a head of a patient and a pair of second recessed portions, each second recessed portion being shaped to receive an arm of the patient, wherein the pair of second recessed portions curve around the first recessed portion and toward each other such that hands of the patient are positioned behind the head and proximate to each other.

17. A support in accordance with claim 16 wherein the plurality of depressions are configured to maintain the head and arms of the patient in a supine position with both arms alongside the head.

18. A support for medical imaging, said support comprising:
   a lower body configured to engage a portion of a medical imaging system; and
   an upper surface extending along the lower body and being shaped to have a plurality of depressions, the plurality of depressions including a first recessed portion shaped to receive a head of a patient and at least one second recessed portion shaped to receive an arm of the patient, wherein the upper surface includes a front end that is sized and shaped to engage at least one shoulder of the patient such that the shoulder of the patient rests on top of the upper surface at the front end.

19. A support in accordance with claim 18 wherein the plurality of depressions and the front end are configured to maintain the arm of the patient above the head of the patient.

* * * * *